(12) United States Patent
Priebe

(10) Patent No.: US 7,662,859 B2
(45) Date of Patent: Feb. 16, 2010

(54) CONTRAST AGENTS

(75) Inventor: Hanno Priebe, Oslo (NO)

(73) Assignee: GE Healthcare AS, Oslo (NO)

( * ) Notice: Subject to any disclaimer, the term of this patent is extended or adjusted under 35 U.S.C. 154(b) by 139 days.

(21) Appl. No.: 12/031,070

(22) Filed: Feb. 14, 2008

(65) Prior Publication Data

US 2008/0199404 A1 Aug. 21, 2008

(30) Foreign Application Priority Data

Feb. 16, 2007 (NO) .................................. 20070913

(51) Int. Cl.
*C07C 275/30* (2006.01)
*A61K 31/175* (2006.01)
(52) U.S. Cl. ........................................ 514/591; 564/38
(58) Field of Classification Search .................. 514/38; 564/591
See application file for complete search history.

(56) References Cited

U.S. PATENT DOCUMENTS

| 4,250,133 A | 2/1981 | Doremus |
| 5,019,370 A | 5/1991 | Jay et al. |
| 5,817,873 A | 10/1998 | Meyer et al. |

FOREIGN PATENT DOCUMENTS

| EP | 108638 | 7/1986 |
| EP | 436316 | 7/1991 |
| EP | 354836 | 1/1993 |
| EP | 782563 | 7/1997 |
| WO | 90/01194 | 2/1990 |
| WO | 91/13636 | 9/1991 |
| WO | 95/01966 | 1/1995 |
| WO | 95/35122 | 12/1995 |
| WO | 98/52911 | 11/1998 |

*Primary Examiner*—Peter G O'Sullivan
(74) *Attorney, Agent, or Firm*—Craig Bohlken

(57) ABSTRACT

The present invention relates to a class of compounds and to diagnostic compositions containing such compounds where the compounds are iodine containing compounds. More specifically the iodine containing compounds are chemical compounds containing an aliphatic central moiety allowing for the arrangement of three iodinated phenyl groups bound thereto.

The invention also relates to methods of diagnosis and imaging employing such diagnostic compositions as contrast agents in particular in X-ray imaging, and to contrast media containing such compounds.

27 Claims, No Drawings

CONTRAST AGENTS

TECHNICAL FIELD OF THE INVENTION

The present invention relates to a class of compounds and to diagnostic compositions containing such compounds where the compounds are iodine containing compounds. More specifically the iodine containing compounds are chemical compounds containing an aliphatic central moiety allowing for the arrangement of three iodinated phenyl groups bound thereto.

The invention also relates to the use of such diagnostic compositions as contrast agents in diagnostic imaging and in particular in X-ray imaging and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™), nonionic monomers such as iohexol (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in mg iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast agents of high molecular weight has been proposed, e.g. polymers with substituted triiodinated phenyl groups grafted on the polymer, see EP 354836, EP 436316 and U.S. Pat. No. 5,019,370. Further, WO 9501966, EP 782563 and U.S. Pat. No. 5,817,873 read on compounds having e.g. 3 and 4 substituted triiodinated phenyl groups arranged linearly or around a central core. However, none of these proposed compounds are on the market.

Hence there still exists a desire to develop contrast agents that solves one or more of the problems discussed above. Such agents should ideally have improved properties over the soluble iodine containing compounds on the market in one or more of the following properties: renal toxicity, osmolality, viscosity, solubility, injection volumes/iodine concentration and attenuation/radiation dose.

SUMMARY OF THE INVENTION

The present invention provides contrast media having improved properties over the known media with regards to at least one of the following criteria osmolality (and hence the renal toxicity), viscosity, iodine concentration and solubility. The contrast media comprises iodine containing contrast enhancing compounds where iodine containing compounds are chemical compounds containing a central aliphatic moiety, allowing for the arrangement of three iodinated phenyl groups bound to thereto. The iodine containing contrast enhancing compounds can be synthesized from commercially available and relatively inexpensive starting materials.

DETAILED DESCRIPTION OF THE INVENTION

The new compounds of the invention, their use as X-ray contrast agents, their formulation and production are specified in the attached claims and in the specification hereinafter.

The contrast enhancing compounds are synthetic chemical compounds of formula (I)

$$A(R)_3 \qquad \text{Formula (I)}$$

and salts or optical active isomers thereof wherein

A denote a moiety of the formula

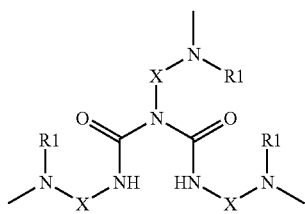

each group X independently of each other are the same or different and denotes an optionally substituted $C_1$ to $C_5$ alkylene moiety;

each group $R^1$ independently of each other are the same or different and denote a hydrogen atom or an aliphatic acyl group; and each R independently of each other are the same or different and denote a triiodinated phenyl group comprising at least one hydrophilic group.

The substituents X above are the same or different. Preferably X denotes hydrophilic alkylene moieties, e.g. alkylene groups substituted with one or more hydroxy groups and optionally interrupted by an oxygen, nitrogen of sulphur atom. Even more preferred all three X-groups are the same and denote hydrophilic moieties. In a particularly preferred aspect of the invention all X-groups are the same and denote a hydroxylated alkylene group such as a 2-hydroxy-propylene moiety.

The $R^1$ groups may also be the same or different. In a preferred embodiment each $R^1$ group may independently of each other denote residues of aliphatic organic acids, and in particular residues of aliphatic organic acids of 1 to 5 carbon atoms such as the formyl, acetyl, propionyl, butyryl, isobutyryl and valeriyl moieties. Hydroxylated and metoxylated acyl moieties are also feasible. In a further preferred embodiment all $R^1$ groups are the same. In a particular preferred embodiment all $R^1$ groups are the same and denote the acetyl moiety.

Each of the iodinated R groups can be the same or different and preferably denote a 2,4,6 triiodinated phenyl group further substituted by two groups $R^2$ in the remaining 3 and 5 positions. Each $R^2$ may also be the same or different and denote a hydrogen atom or a non-ionic hydrophilic moiety, provided that at least one $R^2$ group in the compound of formula (I) is a hydrophilic moiety.

Preferably all three R groups in the compound of formula (I) are the same, and even more preferred each substituent R have two hydrophilic moieties which may be the same or different.

The non-ionic hydrophilic moieties may be any of the non-ionizing groups conventionally used to enhance water solubility. Hence, the $R^2$ substituents may be the same or different and shall preferably all denote a non-ionic hydrophilic moiety comprising esters, amides and amine moieties, optionally further substituted by a straight chain or branched chain $C_{1-10}$ alkyl groups, preferably $C_{1-5}$ alkyl groups, where the alkyl groups also may have one or more $CH_2$ or CH moieties replaced by oxygen or nitrogen atoms. The $R^2$ substituents may also further contain one or more groups selected from oxo, hydroxyl, amino or carboxyl derivative, and oxo substituted sulphur and phosphorus atoms. Each of the straight or branched alkyl groups preferably contains 1 to 6 hydroxy groups and more preferably 1 to 3 hydroxy groups. Therefore, in a further preferred aspect, the $R^2$ substituents are the same or different and are mono or polyhydroxy $C_{1-5}$ alkyl, hydroxyalkoxyalkyl with 1 to 5 carbon atoms and hydroxypolyalkoxyalkyl with 1 to 5 carbon atoms, and are attached to the iodinated phenyl group via an amide or a carbamoyl linkage, preferably amide linkages.

The $R^2$ groups of the formulas listed below are particularly preferred:
—$CONH$—$CH_2$—$CH_2$—$OH$
—$CONH$—$CH_2$—$CHOH$—$CH_2$—$OH$
—$CON(CH_3)CH_2$—$CHOH$—$CH_2OH$
—$CONH$—$CH$—$(CH_2$—$OH)_2$
—$CON$—$(CH_2$—$CH_2$—$OH)_2$
—$CONH_2$
—$CONHCH_3$
—$CONH$—$CH_2$—$CH_2$—$O$—$CH_3$
—$CONH$—$O$—$CH_3$
—$CONH$—$CH_2$—$CHOH$—$CH_2$—$O$—$CH_3$
—$CONH$—$CH_2$—$CHOCH_3$—$CH_2$—$OH$
—$CON(CH_2$—$CHOH$—$CH_2$—$OH)(CH_2$—$CH_2$—$OH)$
—$CONH$—$C(CH_2$—$OH)_2CH_3$
—$CONH$—$C(CH_2$—$OH)_3$
—$CONH$—$CH(CH_2$—$OH)(CHOH$—$CH_2$—$OH)$
—$NHCOCH_2OH$
—$N(COCH_3)H$ —N(COCH$_3$)C$_{1-3}$alkyl
—N(COCH$_3$)-mono, bis or tris-hydroxy C$_{1-4}$ alkyl
—N(COCH$_2$OH)-hydrogen, mono, bis or tris-hydroxy C$_{1-4}$ alkyl
—N(CO—CHOH—CH$_2$OH)-hydrogen, mono, bis or trihydroxylated C$_{1-4}$ alkyl.
—N(CO—CHOH—CHOH—CH$_2$OH)-hydrogen, mono, bis or trihydroxylated C$_{1-4}$ alkyl
—N(CO—CH—(CH$_2$OH)$_2$)-hydrogen, mono, bis or trihydroxylated C$_{1-4}$ alkyl and
—N(COCH$_2$OH)$_2$.

Even more preferably the R$^2$ groups will be equal or different and denote one or more moieties of the formulas —CONH—CH$_2$—CHOH—CH$_2$—OH, —CON(CH$_3$)CH$_2$—CHOH—CH$_2$OH, —CONH—CH—(CH$_2$—OH)$_2$, —CON—(CH$_2$—CH$_2$—OH)$_2$, —CONH—CH$_2$—CH$_2$—OH, —CONH—O—CH$_3$, and —CONH—CH$_2$—CHOH—CH$_2$—O—CH$_3$. Still more preferably all R$^2$ groups are equal and denote one of these moieties.

In a preferred embodiment all R, R$^1$ and X groups in the chemical compound of formula (I) are the same.

One preferred structure according to the invention includes the compounds of formula (II):

(Formula II)

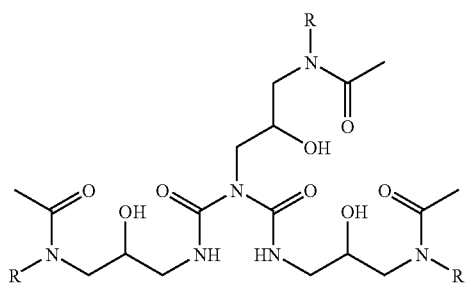

In formula (II), the group A of formula (I) denotes a dicarbonimidic diamide residue tri-substituted by the moieties —CH$_2$—CHOH—CH$_2$—N(acetyl)-R wherein the R groups are equal and denote 2,4,6-triiodinated phenyl groups further substituted by two hydrophilic groups R$^2$.

Particularly preferred is the compound of formula (III):

Formula (III)

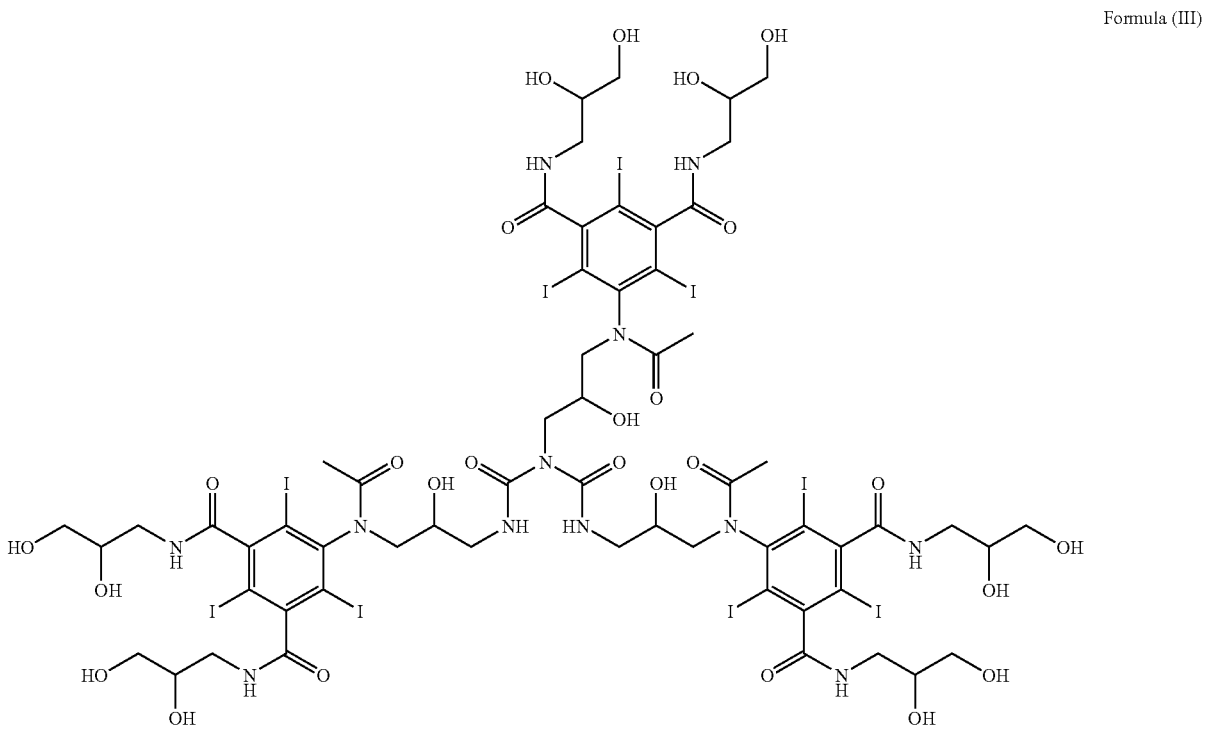

The compounds of formula (I) may attain a star-form with the relatively bulky iodinated phenyl substituents filling up the area between the 3 arms of the star. The molecule will therefore adopt a relatively round or globular form. Globular molecules will usually have enhanced solubility compared with similar molecules with a more planar structure.

At an iodine concentration of 320 mg/ml, which is a common concentration for commercially available iodinated contrast media, the concentration of the compound of formula (I) will be approximately 0.28 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises optical active isomers. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

In a further embodiment the invention provides diagnostic agents comprising a compound of formula (I) and diagnostic compositions comprising a compound of formula (I) together with pharmaceutically acceptable carriers or excipients. The diagnostic agents and composition are preferably for use in X-ray diagnosis.

The contrast media containing compounds of formula (I) can be administered by injection or infusion, e.g. by intervascular administration. Alternatively, contrast media containing compounds of formula (I) may also be administered orally. For oral administration the contrast medium may be in the form of a capsule, tablet or as liquid solution.

Hence, the invention further embraces use of a diagnostic agent and a diagnostic composition containing a compound of formula (I) in X-ray contrast examinations and use of a compound of formula (I) for the manufacture of a diagnostic composition for use as an X-ray contrast agent.

A method of diagnosis comprising administration of compounds of formula (I) to the human or animal body, examining the body with a diagnostic device and compiling data and images from the examination is also provided. In the method of diagnosis the body may also be preadministrated with compounds of formula (I).

Furthermore, a method of imaging, specifically X-ray imaging is provided, which comprises administration of compounds of formula (I) to the human or animal body, examining the body with a diagnostic device and compiling images and data from the examination and optionally analysing the images and data. In the method of imaging the body may also be preadministrated with compounds of formula (I).

Preparation

The compounds of the general formula (I) can be synthesized from triepoxide derivatives of cyanuric acid and triiodinated phenyl compounds having a reactive amine function followed by selective solvolysis of the cyanuric acid in a in a four step/one pot process. The Tris-(2,3-epoxypropyl)isocyanurate is commercially available.

Tri-iodinated phenyl compounds are commercially available or can be produced following procedures described or referred to e.g. in WO95/35122 and WO98/52911. The preferred tri-iodinated compound 5-amino-2,4,6-triiodo-N,N'-bis(2,3-dihydroxypropyl)-isophtalamide is commercially available e.g. from Fuji Chemical Industries, Ltd. The corresponding 5-N-acetylated compound can be produced by acetylation with acetic acid anhydride, e.g. as described in U.S. Pat. No. 4,250,113.

In the preparation of the compounds of the invention, the acylamino-triiodophenyl derivate is dissolved in aqueous alkanol in the presence of alkali hydroxide. Methanol is the preferred alkanol solvent. Optionally the start pH can be adjusted with boric acid before addition of the alkylating isocyanurate derivative. Selective solvolysis of the isocyanurate ring can be achieved by suitable high reaction temperature and corresponding long reaction time as further illustrated in the Example. The reaction is stopped by neutralisation to pH<7 and the product is isolated by preparative HPLC.

The process for the preparation is conducted as a one pot process without isolation of the intermediates and represents a further embodiment of the invention.

The process procedure can be illustrated by the scheme below, where a compound of formula (III) of Example 1 is produced:

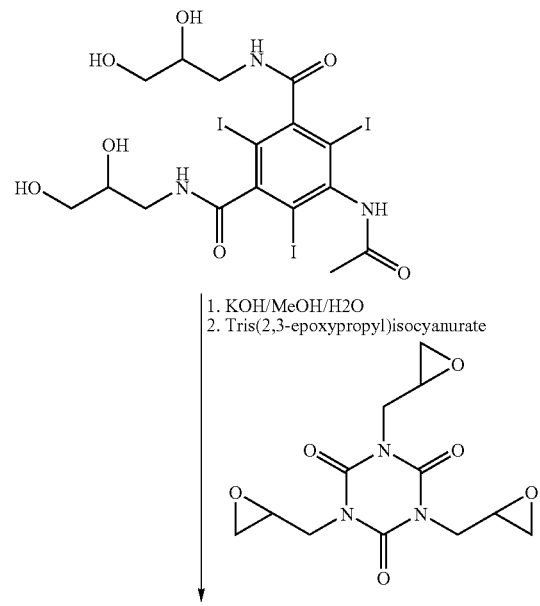
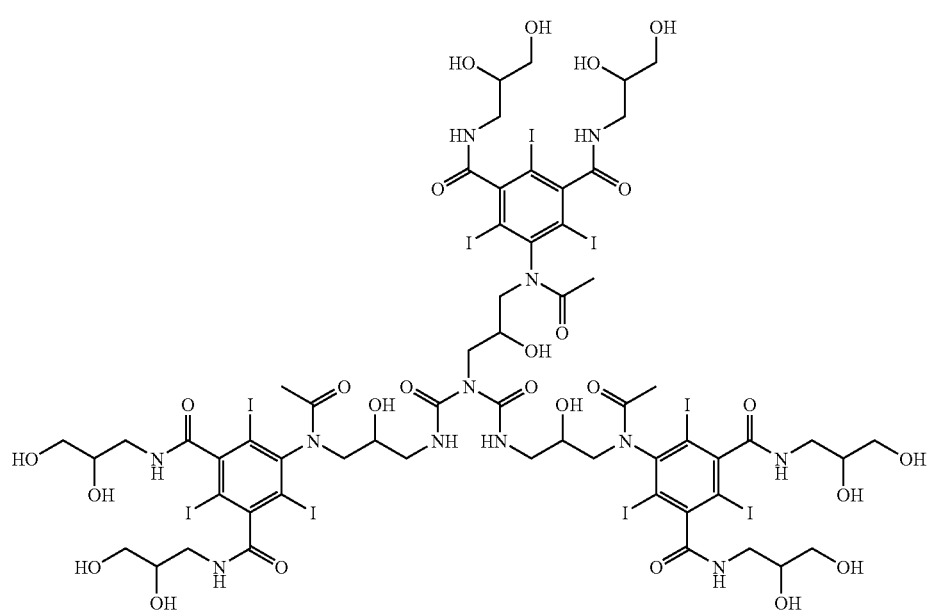
Formula (III)

EXAMPLE 1

N,N,N'-tris-(3-{acetyl-[3,5-bis-(2,3-dihydroxy-propyl-carbamoyl)-2,4,6-triiodo-phenyl]-amino}-2-hydroxy-propyl)-dicarbonimidic diamide At 23-50° C. 5-Acetylamino-N,N'-bis-(2,3-dihydroxypropyl)-2,4,6-triiodo-isophthalamide (400 g, 535.4 mmol) was dissolved in a solution of KOH (46.2 g, 823.8 mmol) in water (432 ml) and methanol (203 ml). To the clear solution boric acid (21.55 g, 348.5 mmol) is added and stirred for 0.5-3 h. At 20-30° C. Tris(2,3-epoxypropyl)isocyanurate (26.85 g, 90.3 mmol) was added and stirred for 1-2 days. The reaction was stopped by adding water (570 ml) and neutralization with 18.4% aqueous HCl to pH 4-5. A white precipitate (starting material) was filtered and the filtercake washed with water. Salts were removed from the filtrate by ion exchangers Amberlite 200C and IRA67. The solution contains 25 HPLC area % target compound (ca. 57 g) and the product was isolated by prep. HPLC.

HPLC/MS (TOF ES+, m/e): 2513.1 [M$^+$], 1268.1 [M$^{2+}$+Na]. $^1$HNMR (d6-DMSO): 6-7 ppm urea NH IR: 3266 (m), 2931 (w), 1634 (s), 1554 (s), 1397 (m), 1259 (s), 1110 (m), 1036 (m), 979 (w).

The invention claimed is:

1. Compounds of formula (I)

A(R)$_3$    Formula (I)

and salts or optical active isomers thereof,
wherein
A denote a moiety of the formula

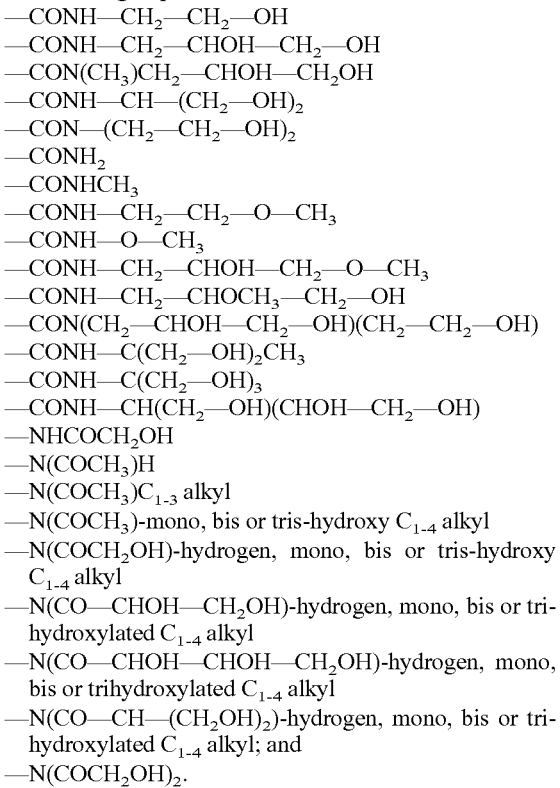

each group X independently are the same or different and denotes an optionally substituted C$_1$ to C$_5$ alkylene moiety;
each group R$^1$ independently are the same or different and denote a hydrogen atom or an aliphatic acyl group; and
each R independently are the same or different and denote a triiodinated phenyl group comprising at least one hydrophilic group.

2. Compounds as claimed in claim 1 wherein X are the same or different and denote hydrophilic alkylene moieties.

3. Compounds as claimed in claim 2 wherein each X are the same and denote hydrophilic moieties.

4. Compounds as claimed in claim 3 wherein each X denote the 2-hydroxy-propylene moiety.

5. Compounds as claimed in claim 1 wherein each of the R$^1$ groups are the same or different and denote residues of aliphatic organic acids.

6. Compounds as claimed in claim 5 wherein each of the R$^1$ groups denote residues of optionally hydroxylated or metoxylated aliphatic organic acids of 1 to 5 carbon atoms.

7. Compounds as claimed in claim 6 wherein each of the R$^1$ groups denote formyl, acetyl, propionyl, butyryl, isobutyryl and valeriyl moieties.

8. Compounds as claimed in claim 5 wherein all R$^1$ groups are the same.

9. Compounds as claimed in claim 1 wherein each R group denote a 2,4,6 triiodinated phenyl group further substituted by R$^2$ groups in the 3 and 5 positions wherein each R$^2$ is the same or different and denote a hydrogen atom or a non-ionic hydrophilic moiety, provided that at least one R$^2$ denotes a hydrophilic moiety.

10. Compounds as claimed in claim 1 wherein each R$^2$ are the same or different and denote a non-ionic hydrophilic moiety comprising esters, amides and amine moieties, optionally further substituted by a straight chain or branched chain C$_{1-10}$ alkyl groups where the alkyl groups optionally have one or more CH$_2$ or CH moieties replaced by oxygen or nitrogen atoms and are optionally substituted by one or more groups selected from oxo, hydroxyl, amino or carboxyl derivative, and oxo substituted sulphur and phosphorus atoms.

11. Compounds as claimed in claim 10 wherein each R$^2$ are hydrophilic moieties containing 1 to 6 hydroxy groups.

12. Compounds as claimed in claim 10 wherein each R$^2$ are the same or different and are mono or polyhydroxy C$_{1-5}$ alkyl, hydroxyalkoxyalkyl with 1 to 5 carbon atoms and hydroxypolyalkoxyalkyl with 1 to 5 carbon atoms, and are attached to the iodinated phenyl group via an amide or a carbamoyl linkage.

13. Compounds as claimed in claim 10 wherein each R$^2$ are selected from groups of the formulas
  —CONH—CH$_2$—CH$_2$—OH
  —CONH—CH$_2$—CHOH—CH$_2$—OH
  —CON(CH$_3$)CH$_2$—CHOH—CH$_2$OH
  —CONH—CH—(CH$_2$—OH)$_2$
  —CON—(CH$_2$—CH$_2$—OH)$_2$
  —CONH$_2$
  —CONHCH$_3$
  —CONH—CH$_2$—CH$_2$—O—CH$_3$
  —CONH—O—CH$_3$
  —CONH—CH$_2$—CHOH—CH$_2$—O—CH$_3$
  —CONH—CH$_2$—CHOCH$_3$—CH$_2$—OH
  —CON(CH$_2$—CHOH—CH$_2$—OH)(CH$_2$—CH$_2$—OH)
  —CONH—C(CH$_2$—OH)$_2$CH$_3$
  —CONH—C(CH$_2$—OH)$_3$
  —CONH—CH(CH$_2$—OH)(CHOH—CH$_2$—OH)
  —NHCOCH$_2$OH
  —N(COCH$_3$)H
  —N(COCH$_3$)C$_{1-3}$ alkyl
  —N(COCH$_3$)-mono, bis or tris-hydroxy C$_{1-4}$ alkyl
  —N(COCH$_2$OH)-hydrogen, mono, bis or tris-hydroxy C$_{1-4}$ alkyl
  —N(CO—CHOH—CH$_2$OH)-hydrogen, mono, bis or trihydroxylated C$_{1-4}$ alkyl
  —N(CO—CHOH—CHOH—CH$_2$OH)-hydrogen, mono, bis or trihydroxylated C$_{1-4}$ alkyl
  —N(CO—CH—(CH$_2$OH)$_2$)-hydrogen, mono, bis or trihydroxylated C$_{1-4}$ alkyl; and
  —N(COCH$_2$OH)$_2$.

14. Compounds as claimed in claim 10 wherein each R$^2$ are equal or different and denote one or more moieties of the formulas —CONH—CH$_2$—CHOH—CH$_2$—OH, —CON(CH$_3$)CH$_2$—CHOH—CH$_2$OH, —CONH—CH—(CH$_2$—OH)$_2$, —CON—(CH$_2$—CH$_2$—OH)$_2$, —CONH—CH$_2$—CH$_2$—OH, —CONH—O—CH$_3$, and —CONH—CH$_2$—CHOH—CH$_2$—O—CH$_3$.

15. Compounds as claimed in claim 10 wherein each R$^2$ are the same.

16. Compounds as claimed in claim 10 wherein each R$^2$ are the same and are —CONH—CH$_2$—CHOH—CH$_2$—OH.

17. Compounds of claim 1 being N,N,N'-tris-(3-{acetyl-[3,5-bis-(2,3-dihydroxy-propyl-carbamoyl)-2,4,6-triiodo-phenyl]-amino}-2-hydroxy-propyl)-dicarbonimidic diamide.

18. A diagnostic agent comprising a compound of formula (I) as defined in claim 1.

19. A diagnostic composition comprising a compound of formula (I) as defined in claim 1 together with a pharmaceutically acceptable carrier or excipient.

20. An X-ray diagnostic composition comprising a compound of formula (I) as defined in claim 1 together with a pharmaceutically acceptable carrier or excipient.

21. A method of diagnosis comprising administration of compounds of formula (I) as defined in claim 1 to the human or animal body, examining the body with a diagnostic device and compiling images of the body or parts thereof.

22. A process for the production of compounds of formula (I) as defined in claim 1 by dissolving an acylamino-triiodophenyl derivate in aqueous alkanol in the presence of alkali hydroxide, optionally pH adjustment with boric acid, addition of the alkylating isocyanurate derivative, and selective solvolysis of the isocyanurate ring wherein the reaction steps are performed as an one-pot process.

23. Compounds as claimed in claim 2 wherein said hydrophilic alkylene moieties are alkylene groups substituted with one or more hydroxyl groups and optionally interrupted by an oxygen, nitrogen or sulphur atom.

24. Compounds as claimed in claim 3 wherein said hydrophilic moieties are hydroxylated alkylene groups.

25. Compounds as claimed in claim 10 wherein said $C_{1-10}$ alkyl groups are $C_{1-5}$ alkyl groups.

26. Compounds as claimed in claim 11 wherein each $R^2$ are hydrophilic moieties containing 1-3 hydroxy groups.

27. Compounds as claimed in claim 12 wherein each $R^2$ is attached via amide linkages.

* * * * *